(12) United States Patent
Barnes et al.

(10) Patent No.: US 9,439,503 B2
(45) Date of Patent: Sep. 13, 2016

(54) SHORT WAVELENGTH VISIBLE LIGHT-EMITTING TOOTHBRUSH WITH AN ELECTRONIC SIGNAL INTERLOCK CONTROL

(71) Applicant: OraLucent LLC, Long Beach, CA (US)

(72) Inventors: Mike Barnes, Dunellon, FL (US); Timothy Lawrence, Long Beach, CA (US); Greg Shepherd, Fruitland Park, FL (US); Mathieu Julien Jean Emile Zastawny, Jersey City, NJ (US); Thomas Jason Dooley, Hoboken, NJ (US)

(73) Assignee: OraLucent, LLC, Long Beach, CA (US)

( * ) Notice: Subject to any disclaimer, the term of this patent is extended or adjusted under 35 U.S.C. 154(b) by 0 days.

(21) Appl. No.: 14/946,929

(22) Filed: Nov. 20, 2015

(65) Prior Publication Data

US 2016/0157597 A1    Jun. 9, 2016

Related U.S. Application Data

(62) Division of application No. 14/464,895, filed on Aug. 21, 2014, now Pat. No. 9,198,502.

(60) Provisional application No. 61/923,381, filed on Jan. 3, 2014, provisional application No. 61/912,260, filed on Dec. 5, 2013.

(51) Int. Cl.
*A46B 15/00*     (2006.01)
*A61N 5/06*     (2006.01)

(52) U.S. Cl.
CPC ....... *A46B 15/0008* (2013.01); *A46B 15/0034* (2013.01); *A46B 15/0036* (2013.01); *A61N 2005/0606* (2013.01)

(58) Field of Classification Search
CPC ............................. A61N 5/06; A46B 15/0036
See application file for complete search history.

(56) References Cited

U.S. PATENT DOCUMENTS 4,944,296 A * 7/1990 Suyama ............. A46B 15/0002
                                                        15/167.1
5,372,501 A * 12/1994 Shalvi .................... A61N 1/322
                                                        132/321

(Continued)

FOREIGN PATENT DOCUMENTS

GB     2 030 855        4/1980   ............. A46B 13/02
JP     02283310 A  *  11/1990

(Continued)

OTHER PUBLICATIONS

"Biohazards of ultraviolet, visible and infrared radiation," Sliney, D.H., J. Occup. Med., 1983, Abstract.

(Continued)

*Primary Examiner* — Lynsey Crandall
(74) *Attorney, Agent, or Firm* — MacCord Mason PLLC (57) ABSTRACT

A short wavelength visible light-emitting toothbrush with an electronic interlock control device preventing operation when the toothbrush is removed from the user's mouth. The electronic interlock control over operation is necessary to prevent accidental eye exposure to the high intensity light source with a wavelength in the range of 400 nm to 500 nm. The light-emitting toothbrush activates upon formation of an electrical circuit between the brush handle in contact with the users hand and the brush head or brush bristles in contact with moisture contained in a human mouth such as saliva or water mixed with toothpaste but deactivates immediately when removed from the mouth, thus protecting the user's eyes from direct exposure to the high power light source contained in the brush-head.

4 Claims, 6 Drawing Sheets

(56) References Cited

U.S. PATENT DOCUMENTS

| | | | |
|---|---|---|---|
| 5,653,591 A | 8/1997 | Loge | 433/118 |
| 5,876,207 A | 3/1999 | Sundius et al. | 433/216 |
| 5,894,620 A | 4/1999 | Polaert et al. | 15/22.1 |
| 6,029,304 A * | 2/2000 | Hulke | A46B 15/0002 15/105 |
| 6,081,957 A | 7/2000 | Webb | 15/105 |
| 6,149,895 A | 11/2000 | Kutsch | 424/53 |
| 6,327,734 B1 | 12/2001 | Meginniss, III et al. | 15/105 |
| 6,623,272 B2 | 9/2003 | Clemans | 433/215 |
| 6,752,627 B2 | 6/2004 | Lin | 433/29 |
| 6,902,397 B2 | 6/2005 | Farrell et al. | 433/29 |
| 7,467,946 B2 | 12/2008 | Rizolu et al. | 433/29 |
| 8,021,148 B2 | 9/2011 | Goodson et al. | 433/29 |
| 8,337,213 B2 | 12/2012 | Puurunen et al. | 434/263 |
| 2002/0039720 A1* | 4/2002 | Marx | A61C 17/26 433/216 |
| 2003/0135940 A1 | 7/2003 | Lev et al. | 15/22.1 |
| 2003/0205492 A1 | 11/2003 | Ferbr et al. | 206/362.2 |
| 2003/0232303 A1 | 12/2003 | Black | 433/29 |
| 2004/0019990 A1* | 2/2004 | Farrell | B08B 7/0057 15/105 |
| 2004/0193236 A1 | 9/2004 | Altshuler et al. | 607/88 |
| 2005/0024953 A1* | 2/2005 | Bertagnolli | A61N 1/36 365/199 |
| 2005/0050658 A1 | 3/2005 | Chan et al. | 15/22.1 |
| 2005/0064371 A1 | 3/2005 | Soukos et al. | 433/217.1 |
| 2005/0175956 A1 | 8/2005 | Russel et al. | 433/29 |
| 2008/0032253 A1 | 2/2008 | Montgomery et al. | 433/29 |
| 2008/0086189 A1* | 4/2008 | Taniguchi | A61C 17/22 607/134 |
| 2008/0131834 A1* | 6/2008 | Shepherd | A46B 9/04 433/29 |
| 2008/0183249 A1* | 7/2008 | Kitagawa | A46B 15/0002 607/79 |
| 2008/0199352 A1* | 8/2008 | Fuller | A61L 2/03 422/22 |
| 2008/0276393 A1 | 11/2008 | Russell et al. | 15/105 |
| 2009/0083924 A1 | 4/2009 | Shepherd et al. | 15/105 |
| 2009/0087813 A1 | 4/2009 | Cai et al. | 433/89 |
| 2009/0188057 A1* | 7/2009 | Kunita | A61C 17/222 15/22.1 |
| 2010/0178252 A1 | 7/2010 | Sagel et al. | 424/9.6 |
| 2010/0239998 A1 | 9/2010 | Snyder et al. | 433/29 |
| 2011/0296643 A1 | 12/2011 | Shepherd et al. | 15/167.1 |
| 2012/0246846 A1 | 10/2012 | Hall | 15/22.1 |
| 2012/0246858 A1 | 10/2012 | De Vries et al. | 15/167.3 |
| 2013/0025078 A1* | 1/2013 | Heil | A61C 17/3436 15/22.1 |
| 2013/0072851 A1* | 3/2013 | Doll | A61N 1/32 604/20 |
| 2013/0137974 A1 | 5/2013 | Sakaguchi et al. | 600/424 |
| 2014/0020198 A1* | 1/2014 | Slocum | A46B 15/0038 15/167.1 |
| 2014/0272768 A1* | 9/2014 | Curry | A61B 5/0088 433/27 |

FOREIGN PATENT DOCUMENTS

| | | | | |
|---|---|---|---|---|
| JP | 08275961 | | 10/1996 | A61C 17/22 |
| JP | 2000/175745 | | 6/2000 | A46B 15/00 |
| JP | 2000175745 A | * | 6/2000 | |
| WO | WO 2009141489 | | 2/2010 | A61C 19/04 |

OTHER PUBLICATIONS

"Effect of light energy on peroxide tooth bleaching," Luk, et al., J.Am. Dent. Assoc, 2004, Abstract.

"External bleaching therapy with activation by heat, light or laser—a systematic review," Buchalla, W., et al., Dent Mater. 2007, Abstract.

"Maximum permissible exposures for ocular safety (ANSI 2000), with emphasis on ophthalmic devices," Delor, et al., J. Opt. Soc. Am. A. Opt Image Sci Vis., 2007, Abstract.

"Genetic and Physiological Effects of Noncoherent Visible Light Combined with Hydrogen Peroxide on *Streptococcus mutans* in Biofilm," Steinberg, et al., Antimicrob. Agents Chemother., Jul. 2008 vol. 52, No. 7 2626-2431.

"Inactivation of Bacterial Pathogens followin Exposure to Light from a 405-Nanometer Light-Emitting Diode Array," Maclean, et al., Appl. Environ. Microbiol. Apr. 2009 75(7).

* cited by examiner

SHORT WAVELENGTH VISIBLE LIGHT-EMITTING TOOTHBRUSH WITH AN ELECTRONIC SIGNAL INTERLOCK CONTROL

This application is a division of application Ser. No. 14/464,895 filed Aug. 21, 2014, which claims the benefit of Provisional Application Ser. No. 61/923,381 filed Jan. 3, 2014, and Provisional Application Ser. No. 61/912,260 filed Dec. 5, 2013.

BACKGROUND OF THE INVENTION

The present invention relates to increasing the safety of a dental hygiene implement such as a light-emitting manual or an electrically operated motorized toothbrush which emits radiation, in the violet and/or blue region of the visible spectrum, between 400 nm and 500 nm, in order to:
- oxidize and destroy potentially harmful bacteria and/or other contaminants or compounds contained within the mouth without harming or destroying human cells;
- exert a phototoxic effect on pathogenic periodontal and oral bacteria such as; *P. Gingivalis* and *F. Nucleatum*, and *S. Mutans;*
- activate a photo catalyst that may be deposited on the teeth and the gums of the person utilizing the toothbrush during normal brushing; and/or
- accelerate the whitening effects of a tooth bleaching agent added to toothpaste or toothgel such as carbamide peroxide or hydrogen peroxide.

The electronic interlock control mechanism in this toothbrush will reduce the possibility of accidental direct eye exposure to high flux visible light radiation emitted from this toothbrush when it is removed from the mouth.

Light-emitting toothbrushes have been developed over the past several years for teeth whitening applications in addition to the known oral hygiene benefits of regular brushing. When combined with a teeth whitening agent such as carbamide peroxide or hydrogen peroxide, studies have shown that light in the 400-500 nm range accelerates the whitening effect of these agents. Wolfgang Buchallaa, Thomas Attina: *External bleaching therapy with activation by heat, light or laser—A systematic review*; Karen Luk, D.D.S.; Laura Tam, D.D.S., M.Sc.; Manfred Hubert, Ph.D.: *Effect of light energy on peroxide tooth bleaching.*

In addition, violet light in the 400 nm-420 nm range has been shown to have a phototoxic effect on pathogenic oral bacteria such as *P. Gingivalis, S. Mutans* and others. Michelle Maclean, Scott J. MacGregor, John G. Anderson, and Gerry Woolsey: *Inactivation of Bacterial Pathogens following Exposure to Light from a 405-Nanometer Light-Emitting Diode Array.* Doron Steinberg, Daniel Moreinos, John Featherstone, Moshe Shemesh, and Osnat Feuerstein: *Genetic and Physiological Effects of Noncoherent Visible Light Combined with Hydrogen Peroxide on Streptococcus mutants in Biofilm.* The inventors have previously shown the use of a Light-emitting Diode (LED) within a toothbrush provides anti-microbial properties of benefit to the oral hygiene of the end-user.

Current light-emitting toothbrushes have a manual on/off switch which activates the light-emitting device. This manual activation mechanism may lead to a safety risk because the user may activate the light and expose his or her eyes to high levels of light that may be harmful to the retina or optic nerve. The potentially harmful properties of visible light and maximum exposure levels are documented in ANSI standards. Francois C. Delori, Robert H. Webb, David H. Sliney: *Maximum permissible exposures for ocular safety (ANSI 2000), with emphasis on ophthalmic devices.* David H. Sliney, M. S.: *Biohazards of Ultraviolet, Visible and Infrared Radiation.* For example, the maximum permissible radiant power (thermal and photo-acoustic) entering a dilated pupil is 1.5×10-4 Watts. This limit would be exceeded if a user were to stare at a 420 nm LED of 250 mW radiant flux at a distance of 10 cm for a period of 0.5 seconds. To prevent accidental eye exposure a special electronic interlock control mechanism has been implemented to keep the optical source turned off if the toothbrush is not inserted in the users mouth and will turn the optical source off immediately if the toothbrush is removed from the mouth prior to completing the brushing cycle.

A toothbrush is typically used in close proximity to the eyes of the user, and if ocular exposure lasts several seconds, eye damage may happen. Furthermore, the ocular safety risk of manually activated light precludes the use of more powerful light-emitting devices such as high-powered LEDs, laser diodes, or vertical cavity surface emitting lasers, which would increase the teeth-whitening and antimicrobial benefits in proportion to the energy delivered. For example, studies show that effective whitening treatments require a minimum energy density of 30-50 J cm$^{-2}$ to produce noticeable shade whitening. However, such energy levels would not be readily achievable with a typical two minute brushing interval using a low-powered LED that would also be safe when directly placed in front of the eyes, even when used over a period of several weeks. Similar limitations exist for the anti-microbial properties of violet light as well.

It is therefore desirable to control the "on" state of the light-emitting device to a time period when it is in use in the oral cavity but to shut "off" this high power light source immediately, when it is removed from the mouth to prevent direct eye exposure. This feature would also extend battery life of a battery operated brush since power is only used to illuminate the light source when in direct contact with the oral cavity.

SUMMARY OF THE INVENTION

The present invention fulfills one or more of these needs in the art by providing a toothbrush having a light source. The brush includes a battery, a short wavelength light source, electronics coupled to the battery and source of light with a wavelength in the range of 400 nm to 500 nm to supply electricity from the battery to the source at current and voltage that causes the source to emit short wavelength light. The brush includes a handle and a distal end that includes bristles and the source of light. At least a portion of the handle and distal end are electrically conductive and electrically connected within the brush to the electronics. A person who uses the toothbrush to brush his or her teeth by grasping the handle and inserting the distal end into his or her mouth completes a signal loop that is sensed by the electronics to turn on the source of light, and removal of the distal end from the mouth breaks the signal loop, rapidly turning off source of light.

Preferably, the source of light emits light in the range about 400 nm to about 420 nm. The electronics preferably includes an ultralow power comparator using CMOS electronics. Preferably, the electronics enables the signal loop, and current in the loop is sensed by the electronics at a detection current threshold below a sub-microampere level at around one volt of potential difference.

The natural conductivity of the human body and conductivity of saliva can be exploited to sense the presence of an electrical circuit between the brush handle being held in the hand of the user through the arm, shoulder, neck and head of the end user and the wet bristles of the toothbrush in contact with mucosal tissue of the mouth or saliva or water present in the mouth of the user. This configuration provides the following advantages over other sensor configurations:

- The anode and cathode of the sensor are physically separated by a sufficient distance to preclude the circuit from being inadvertently activated by a wet hand or finger being placed across the sensor and sensor return or by placing the brush head under running water.
- The activation of the sensor through contact with the wetted bristles of the brush allows the light to be activated when the brush head is outside the mouth with only the tips of the bristles in the mouth in contact with the front teeth "incisors." The light can affect the front "incisor" teeth, which are the most important teeth for cosmetic whitening.
- The signal loop sensor in this application is not intended for convenience of automated on/off control; it is a safety feature to prevent accidental eye exposure to high flux blue/violet radiation. A capacitive sensor would not work as well for this application because a capacitive sensor would be triggered by proximity but not necessarily physical contact. A capacitive sensor would potentially turn on the light if the brush head is located close to the moisture of the open eyes, triggering an unintended "on" state causing discomfort or even eye damage to the end user.

In one embodiment the safety feature may be used in combination with a manual on or start switch located in the handle of the brush, such that the light turns on only after the manual start switch is depressed and the interlock sensor loop is completed through contact of the brush head with the mouth.

The invention can also be considered as a method of treating teeth including grasping a toothbrush with the user's hand, inserting bristles of the toothbrush into the mouth of the user, thereby completing an electrical circuit to complete a signal path between the user's hand and the user's mouth to allow the light to impinge on the teeth when the bristles are in the mouth. In one embodiment the signal path passes an electrical current in the range of 10 and 100 nanoamperes. The signal enables activation of a source of light with a wavelength in, preferably, the range of 400 nm to 500 nm in the user's mouth to illuminate the inside of the user's mouth with short wavelength light. The flow of the electrical current stops upon removal of the bristles from the mouth of the user, deactivating the source of light.

In one embodiment, this safety feature can be used in combination with a manual on/off switch, such that the light becomes activated only when the manual switch is "on" and the sensor is also activated through contact of the brush head with the mouth. In an electric motorized brush, such as a sonic or electric spin brush, the manual on/off switch can turn on the motor as well as the light as described above.

BRIEF DESCRIPTION OF THE DRAWINGS

The invention will be better understood by a reading of the Detailed Description of the Examples of the Invention along with a review of the drawings, in which.

DETAILED DESCRIPTION OF EXAMPLES OF THE INVENTION

A light-emitting oral care instrument activates upon the completion of an electrical circuit between the brush handle in contact with the user's hand and contact of the brush head with the user's mouth.

Aspects of the invention are illustrated in the remainder of this disclosure with reference to a manual or electric motorized toothbrush, although it is understood that the operation of any number of light-emitting oral care instruments, together with the associated advantageous features and/or beneficial effects described herein, could likewise be achieved. Other oral care instruments may include those used in dental curing lamps, oral flossing implements, and oral surgical instruments, etc.

Many electric toothbrushes employ a timer to alert the user of the end of a preset brushing time, for example, two minutes, as recommended by the American Dental Association. These timer circuits are commonly combined with vibration or noise to alert the end user to the completion of a recommended brushing period. The signal loop sensor disclosed herein can be combined with such a timing circuit in a manner that causes elapsed time to be recorded only when the sensor is activated (i.e. light is on). This would facilitate the assurance that the brush timer was actually measuring elapsed time in the mouth of the user and not simply elapsed time of the manual activation of the brush.

Figure 1:
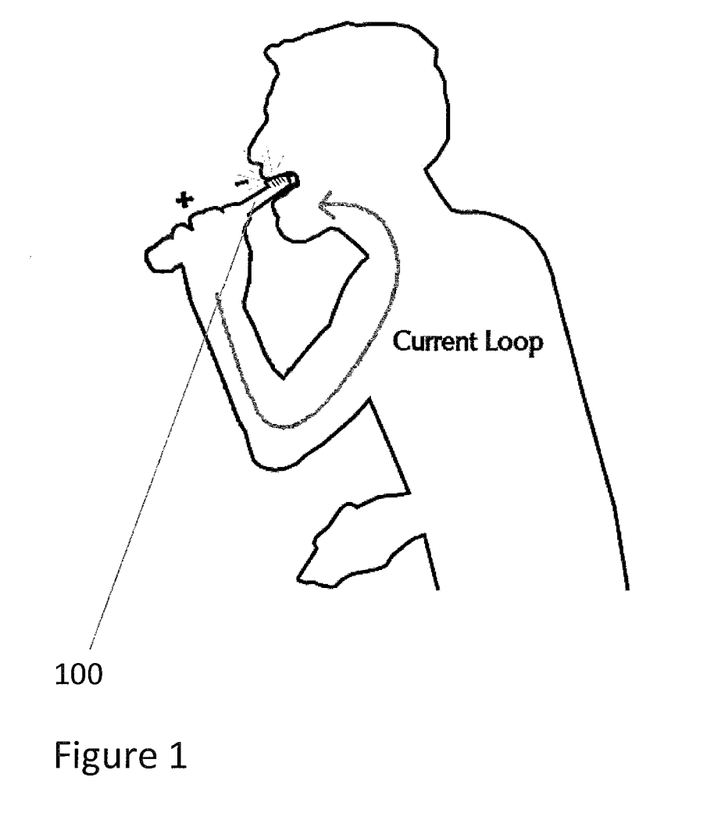
FIG. 1 shows the completion of a signal loop by a user inserting a toothbrush into his mouth.
Figure 2:
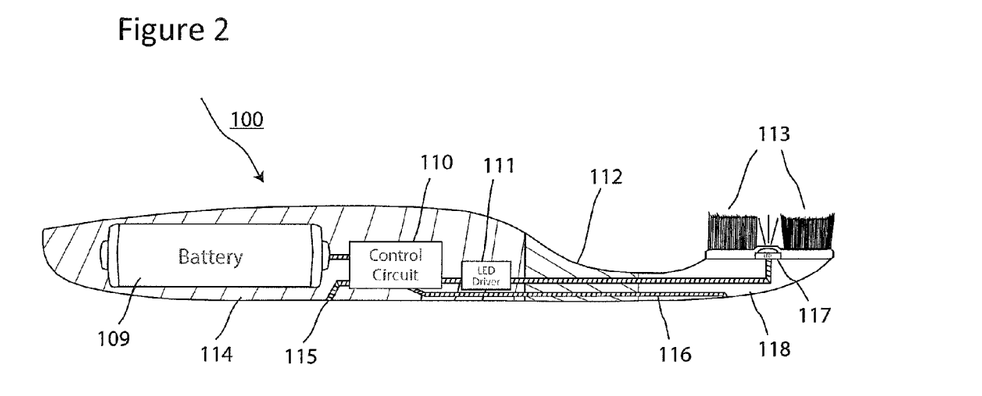
FIG. 2 depicts a representative oral care instrument, a toothbrush, illustrating various aspects.

In the embodiment of the light-emitting toothbrush 100 shown in FIG. 2, the brush head 118 and the handle 114 are injection molded of an electrically-conductive plastic with a non-conductive hydrophobic plastic spacer 112 located between the brush head 118 and the handle 114. The nonconductive plastic spacer 112 electrically insulates the brush head 118 and the handle 114 from each other. The brush head 118 and handle 114 are electrically connected, via a lead 116, to a control circuit 110 that can produce a low level electrical signal. While DC current is likely easiest with a battery source, the signal could be AC. The control circuit 110 can include a high sensitivity current sensor, such as Linear Technology LTC1440 Ultralow Power Single/Dual Comparator with Reference located on the control circuit 110. That comparator is available from Linear Technology Corporation, 1630 McCarthy Blvd., Milpitas, Calif. 95035-74171 (408) 432-1900, linear-tech.com.

Figure 6:
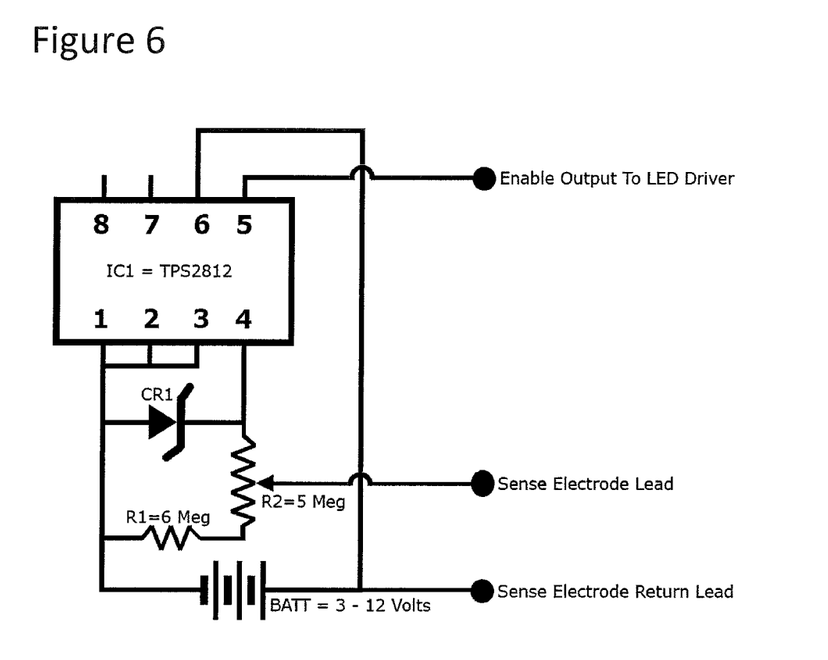
FIG. 6 is a schematic of an exemplary control circuit.

Alternatively, the signal loop sensor circuit can be the one seen in FIG. 6, implemented with off the shelf components. An integrated circuit, IC1 shown in FIG. 6 can be a TPS2812 Dual High-Speed Mosfet Driver available from Texas Instruments, Inc. of Dallas, Tex. One of the sensor electrodes 116 is connected through a battery supplying from three to twelve volts, to pins 1-3 and 6 of IC1. The other sensor electrode 115 is connected across and adjustment bridge variable resistor R2 and to pin 4 of IC1 across resistor R1 to pins 1-3. Pin 4 is tied through Zener diode CR1 to pins 1-3. Pin 5 of IC1 is tied as the output to the LED driver. When the signal loop through electrodes 115 and 116 is completed, the current is sensed in IC1, outputting a signal on pin 5 to activate the driver for the LED.

Prior art toothbrush sensors were implemented with older bipolar transistor technology and required high currents in the signal loop and higher voltages, producing undesirable tingling sensations for the user. The preferred signal loop sensor uses ultra-low-power CMOS technology to reduce the detection current threshold to a sub-microampere level at around one volt of potential difference, preventing any tingling sensation. Another advantage is an ultra-low battery consumption current.

A signal loop is formed through the body of the user by holding the brush handle 114 and placing the brush head 118 or wet bristles of the brush 113 in contact with the mouth. A voltage across the handle and the brush head results in a small signal current that flows through the loop and is detected by the current sensor. The current sensor outputs a signal through the control circuit 110 to the LED driver 111, which delivers current to the LED 117 within the user's mouth, causing the LED 117 to illuminate the mouth of the user. The LED preferably emits short wave length light in the band between 400-500 nm, more preferably 400-450 nm, and more preferably yet of 400-420 nm.

Figure 3:
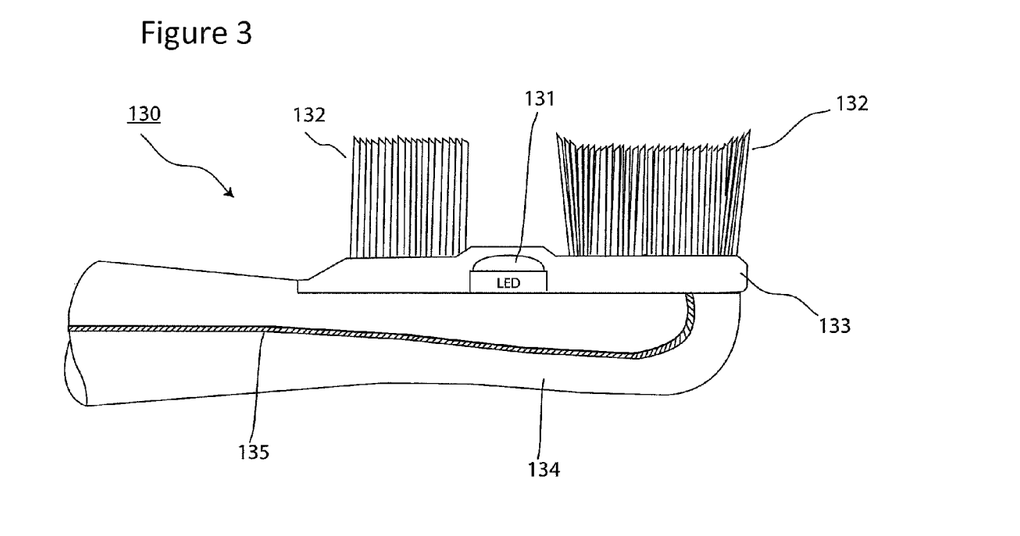
FIG. 3 depicts an alternate embodiment in which the wet bristles of the brush head are conductive to form a contact for completion of the signal loop.

In an alternate embodiment 130 shown in. FIG. 3, conductive plastic is used in the part 133 of the brush connecting the bristles 132 to a sheet of conductive plastic 133, instead of the entire brush head. Alternatively, but also possibly in combination, as shown in FIG. 3, the bristles 132 of the brush may also be conductive. When wet bristles 132 come in contact with the mouth of the user during normal brushing operations a circuit is formed via a sense electrode 135 connected to the control circuit 110, which can be used to detect the completion of the electrical signal loop and signals the driver 111 to supply electricity to the LED 131. The remainder of the brushhead 134 is composed of non-conductive plastic.

Typically when brushing teeth, a user will grasp the handle 114 of toothbrush 100, apply toothpaste to the bristles 113 and place the brush head 118 in the mouth and proceed to brush their teeth. While the toothbrush handle 114 is in contact with the user's hand and the brush head 118 is located in the mouth of the user, contact between the electrically conductive plastic of the brush head 118 and mouth of the user completes the signal loop, enabling a small DC or AC current (sensor current) to be initiated and detected by the control circuit 110. The receipt of the sensor current is signaled to the LED driver which, in turn, controls illumination of the LED 117, in this case, turns on the LED 117. When contact between the brush head 118 and the mouth is broken, i.e., when the brush head 118 is withdrawn from the mouth, the signal loop is broken, the flow of sensor current stops, and the LED 117 is turned off. It is to be appreciated that the sensor current required to control the LED 117 will preferably be in the 10 and 100 nanoampere range and would only be detectable with a high sensitivity current meter associated with the control circuitry 110. Due to the use of such a low electrical current, the user will be safe from harm and will not be exposed to danger. The galvanic current generated when a person touches a wet metal object is far greater than the current used in our application, so the current passing through the user's body is harmless and imperceptible.

The electronics, i.e. the LED driver and control circuitry 110 are configured to regulate or adjust the sensor current so that the brush head 118 must be in contact with the user's mouth to turn on the LED 117. Merely contacting the dry skin from hand to hand will not turn the LED 117 on since the dry hand is not as conductive as the wet mouth. This reduces the possibility of turning the LED 117 on merely by handling the toothbrush 100 with bare hands and inadvertently activating the LED 117 while the brush head 118 is not in the user's mouth.

Figure 4:
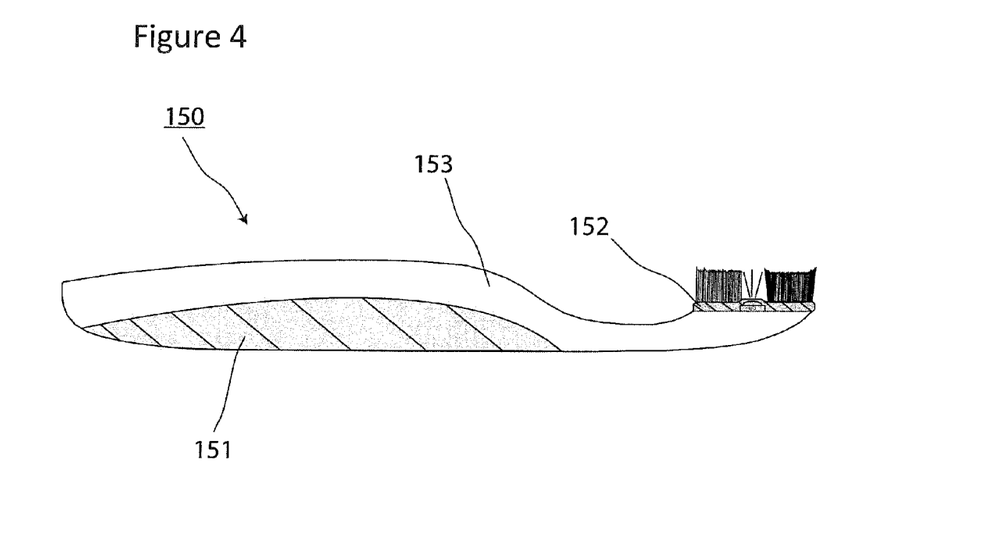
FIG. 4 shows a toothbrush with conductive metal pads.

In a further embodiment of the toothbrush 150 as illustrated in FIG. 4 which is similar to the prior embodiment, the brush head and handle 153 could be formed from a hydrophobic, nonconductive plastic instead of the electrically conductive plastic. In this embodiment, electrically conductive metal pads 151, 152 are located on the exterior surface of the toothbrush 150. One or more metal pads 151 are located on the handle 112' and one or more metal pads 152 are located on the brush head. The metal pads 151 are positioned on the toothbrush 150 for optimal contact with the skin of the hand and pad 152 is mounted for contact with the mouth or bristles of the toothbrush. When the wet tips of the brush bristles are in contact with incisor teeth or mouth and the pad 151 is in contact with the user's hand, an electrical circuit is formed through the body of the user. It is to be understood that the metal pads 152 of the brush head should be spaced apart from the metal pads 151 of the handle.

In use, while the metal pads 151 of the toothbrush handle are in contact with the user's hand and when the brush head 152 is located in the mouth of the user or wet bristles are in contact with any wet portion of the mouth or teeth, contact between the metal pads 152 of the brush head and mouth of the user completes a signal loop, enabling a small DC current (sensor current) to be initiated and detected by the control circuit 110. The sensed current causes the control circuit to activate the LED driver to turn on the LED 126. When contact between the brush head and the mouth is broken, i.e., when the brush head is withdrawn from the mouth, the signal loop is broken, the flow of sensor current stops, and the control circuit turns off.

Figure 5:
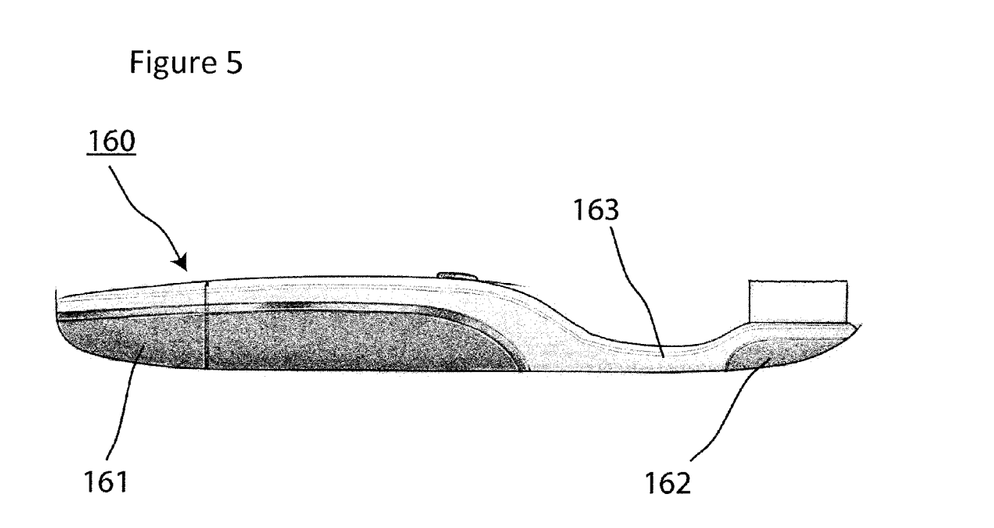
FIG. 5 shows a toothbrush with conductive plastic pads.

A further embodiment 160 is shown in FIG. 5. The handle has a portion 161 of conductive plastic, and the head has a portion 162 of conductive plastic. Portion 163 is non-conductive. The conductive plastic areas are connected internally to circuits as described in connection with FIG. 2, so the toothbrush of FIG. 5 can be used in like manner to the toothbrush of FIG. 2.

The control circuit can also include a timer to turn off the LED at a preset time, such as two minutes, signaling to the user that tooth brushing has lasted two minutes, a sufficient amount of time. Other ways to signal the user of the completion of two minutes can be substituted.

A conventional make/break switch can be included in one of the conductors 115 or 116 or elsewhere in the electrical circuit, if desired. Thus, the signal loop is completed only if the user closes that switch AND inserts the toothbrush head into the mouth. This can provide a further safety and convenience feature. Alternatively, a make/break switch could be located elsewhere in the circuit from the battery, to the control circuit through the LED driver to LED.

Since the LED will be on only when the light from the LED is safely and effectively used, the life of a charge on the battery should be longer.

The battery can be rechargeable or replaceable, as will be apparent to those of ordinary skill in the art.

The brush head and/or neck can be replaceable, as long as the replacement part has the correct electrical contact and a conductor that can reliably connect to a mating conductor in the brush handle. The design can allow the sensor current to flow across the junction of the permanent part and the replaceable part through either two sheets of conducting plastic or a metal connector such as a pin connector. Examples are seen in FIGS. 7 and 8.

Figure 7:
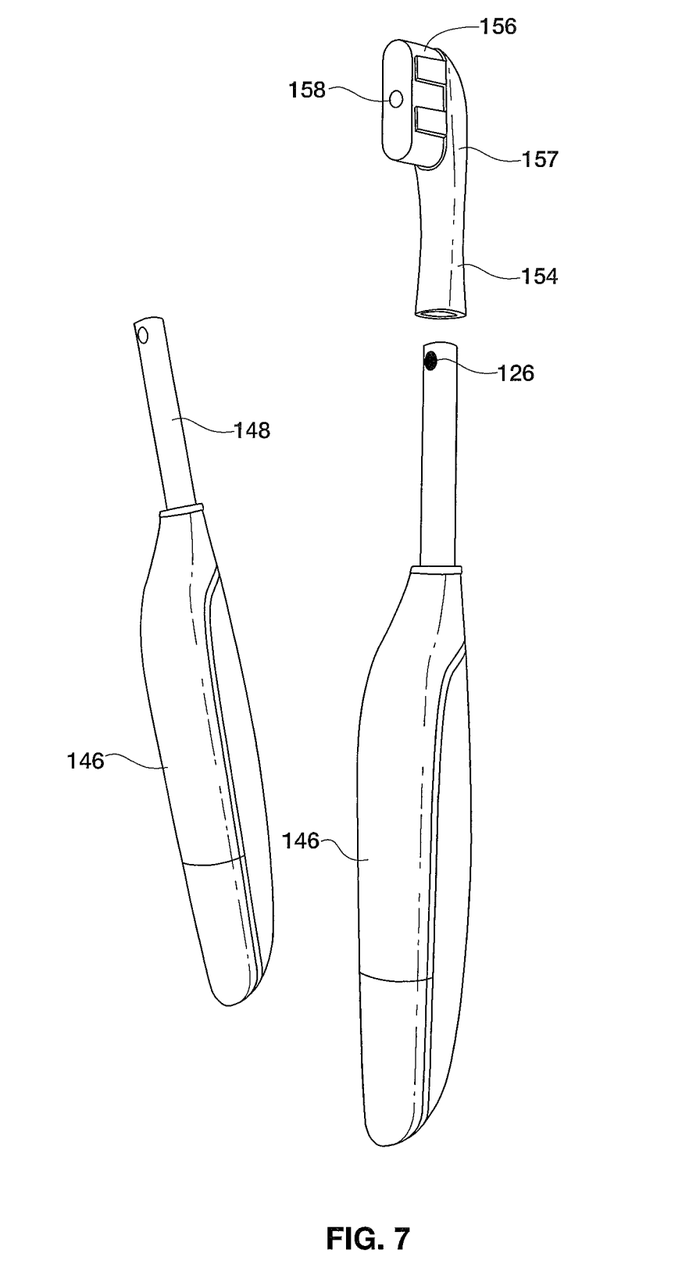
FIG. 7 is a schematic of an exemplary oral care instrument that has a replaceable head and neck.
Figure 8:
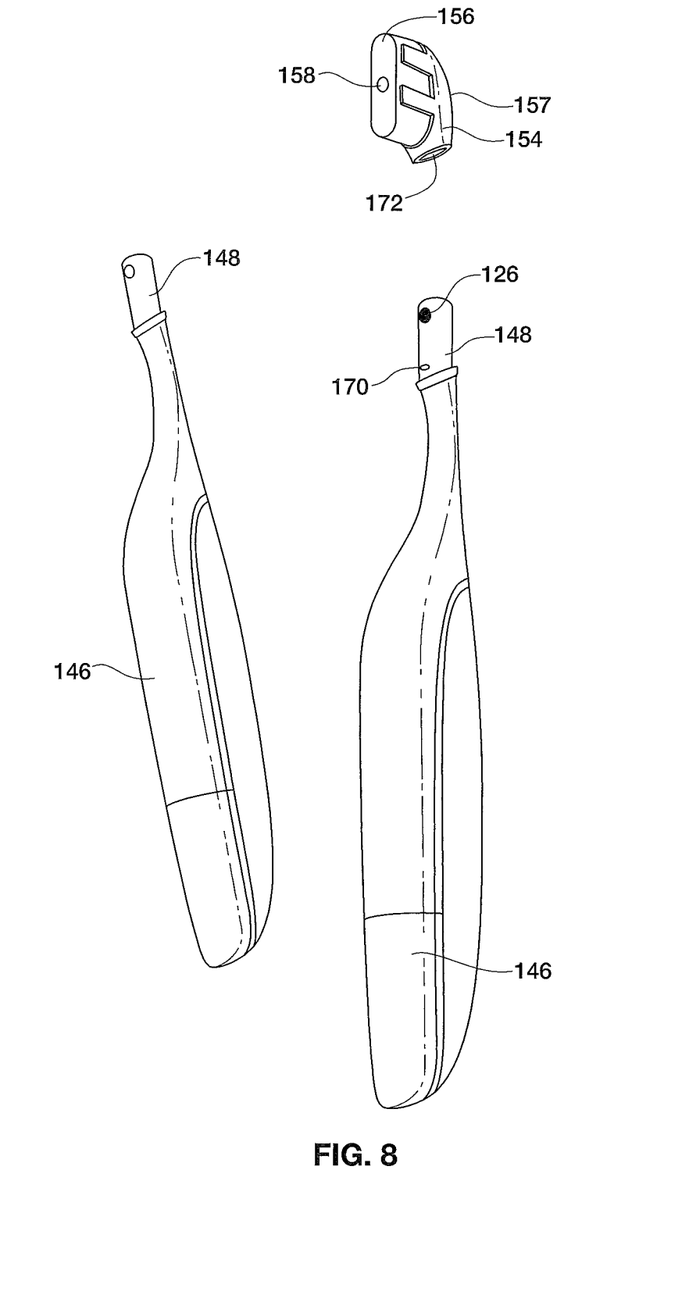
FIG. 8 is a schematic of an exemplary oral care instrument that has a replaceable brush head.

As seen in FIGS. 7 and 8, a brush handle 146 is provided having the necessary battery, charging electronics and LED, all self-contained and water-tightly encapsulated within the handle. The handle includes a stem 148 in which the LED 126 is mounted. FIGS. 7 and 8 show two different embodiments, with the stem 148 in FIG. 7 being longer than the stem 148 of FIG. 8. The replaceable brush head 157 has a hollow shaft 154 of an internal diameter slightly larger than the diameter of the stem 148, so the stem 148 can be inserted into the hollow shaft 154. The brush head has an array of bristles 156 and an opening 158 to allow the light from the LED 126 to pass toward the teeth as they are brushed by the bristles. Preferably the stem and hollow shaft have complementary, non-circular shapes so that the bristles do not rotate around the stem, but stay in a fixed orientation. When the bristles are spent, the brush head 157 can be removed from the stem 148 and replaced with a new brush head. Other appliances appropriate for a tooth whitening brush pattern, light curing of gum infections, tongue scraper, flosser, etc can be configured with similarly shaped hollow shafts so they can also be mounted onto the stem 148.

In the embodiment shown in FIG. 7 the plastic of the stem 148 and the head 157 are made electrically conductive, so that the signal loop can be completed as the user puts the head 157 (as installed on the stem 148) into his or her mouth and grasps the handle 146.

In the embodiment shown in FIG. 8 a conductor in the plastic of the stem 148 has an electrical contact 170; the head 157 has an electrical contact 172 within the shaft 154 positioned to mate with contact 170 when the head is mounted on the stem. The signal loop can be completed as the user puts the head 157 (as installed on the stem 148) into his or her mouth and grasps the handle 146.

A further enhancement of the interlock control feature of this toothbrush can be realized using an AC control signal in place of the DC loop sensor current. A low-frequency 200 Hz to 10 kHz square or sinusoidal waveform AC signal with a peak to peak voltage of no greater than 1 V will be applied to the toothbrush handle. This AC signal will be conducted through the user's body in much the same way as a DC current, as described above. One way to implement this is through selective tone filtering in which a Controlled Oscillator in the handle puts off a square wave form in the low audio band of 1 to 2 kHz. A narrow band tone filter only allows one tone to come through in the brush head. This Selective Tone Filter in the brush head is looking for one certain tone. When it receives that tone, it turns on the LED.

Certain modifications and improvements will occur to those skilled in the art upon reading the foregoing description. It should be understood that all such modifications and improvements have been omitted for the sake of conciseness and readability, but are properly within the scope of the following claims.

What is claimed is:

1. A method of treating teeth comprising:
    Providing a toothbrush, wherein the toothbrush comprises bristles, an electrical circuit and a light source configured to emit light at a wavelength in the range of 400 nm to 500 nm;
    Grasping the toothbrush with a hand of a user;
    Inserting the bristles of the toothbrush into a mouth of the user and thereby completing a signal loop through the hand of the user, the electrical circuit and the mouth of the user;
    Flowing current from the toothbrush through the hand and mouth of the user, due to the completion of the signal loop; wherein the current is in the range of 10 to 100 nanoamperes;
    Activating the light source, due to the flow of current;
    Illuminating an inside of the user's mouth with the light from the light source.

2. A method as claimed in claim 1 further comprising removing the bristles from the mouth of the user, thereby disabling the flow of the electrical current from the toothbrush through the hand and mouth of the user as connected by the user's body and deactivating the source of light.

3. A method as claimed in claim 1 further comprising a step of closing a make/break switch on the brush to enable operation by making a current path through the switch prior to inserting the bristles into the mouth of the user.

4. A method as claimed in claim 1 comprising terminating brushing when a signal is received from the brush that a time period has elapsed.

* * * * *